(12) United States Patent
Manzano Riera

(10) Patent No.: US 8,376,188 B2
(45) Date of Patent: Feb. 19, 2013

(54) DEVICE FOR THE APPLICATION OF FIBRIN ADHESIVE

(75) Inventor: Jorge Maria Manzano Riera, Barcelona (ES)

(73) Assignee: Grifols, S.A., Barcelona (ES)

( * ) Notice: Subject to any disclaimer, the term of this patent is extended or adjusted under 35 U.S.C. 154(b) by 331 days.

(21) Appl. No.: 12/759,954

(22) Filed: Apr. 14, 2010

(65) Prior Publication Data

US 2010/0312274 A1    Dec. 9, 2010

(30) Foreign Application Priority Data

Jun. 9, 2009  (ES) .................................. 200930290

(51) Int. Cl.
*B67D 7/70*  (2010.01)
(52) U.S. Cl. ........................................ 222/137; 606/213
(58) Field of Classification Search .......... 606/213–215; 222/94, 135–137, 386, 325–327, 145.5–145.6; 604/82–85, 191, 218, 224
See application file for complete search history.

(56) References Cited

U.S. PATENT DOCUMENTS

| | | | |
|---|---|---|---|
| 4,359,049 A | | 11/1982 | Redl et al. |
| 4,392,589 A | * | 7/1983 | Herold .......................... 222/137 |
| 4,631,055 A | * | 12/1986 | Redl et al. ........................ 604/82 |
| 4,735,616 A | | 4/1988 | Eibl et al. |
| 6,234,994 B1 | * | 5/2001 | Zinger ............................ 604/82 |
| 6,889,872 B2 | * | 5/2005 | Herman et al. .................. 222/82 |
| 2002/0032463 A1 | * | 3/2002 | Cruise et al. .................. 606/214 |
| 2006/0191962 A1 | | 8/2006 | Redl et al. |
| 2009/0131886 A1 | | 5/2009 | Liu et al. |
| 2009/0152305 A1 | * | 6/2009 | Redl et al. ..................... 222/386 |

FOREIGN PATENT DOCUMENTS

WO   WO 03/039375 A2   5/2003
WO   WO 03/101309 A1   12/2003

OTHER PUBLICATIONS

Spanish Search Report dated Dec. 21, 2009.
European Search Report dated Sep. 28, 2010, issued in the corresponding European Patent Application No. 10380044.7.

* cited by examiner

*Primary Examiner* — Ryan Severson
*Assistant Examiner* — David Eastwood
(74) *Attorney, Agent, or Firm* — RatnerPrestia

(57) ABSTRACT

A device for the application of two components of fibrin adhesive at a treatment site comprising a support for syringes comprising two parallel cylindrical housings to receive corresponding syringes and a plunger connecting member, characterised in that the said syringe support comprises a passage for insertion of the said plunger connecting member, the said passage being located in the space defined between the cylindrical housings of the said syringe support, the said plunger connector having a zone with a suitable geometry to slide within the said passage and in that the transverse cross-section of the said passage of the syringe support has a maximum opening at the ends and a minimum opening in the central part.

20 Claims, 8 Drawing Sheets

DEVICE FOR THE APPLICATION OF FIBRIN ADHESIVE

This invention relates to a device for the application of two compounds, such as the components of fibrin adhesive, in medical and/or hospital environments. More particularly this invention relates to a device which comprises a support for syringes and a member which connects the plungers of the syringes and is sufficient to receive two syringes which separately expel two components of an adhesive, such as fibrinogen and thrombin, in such a way that these subsequently mix in an outlet body and coagulate to seal a wound, staunch bleeding or the like.

Suture has for a long time been the normal method of repairing tissues and wounds in surgery. But the most sophisticated techniques and materials used in sutures are not always sufficient to prevent complications. Furthermore, the suturing of fistulas and granulomas, or sections through parenchymatous organs or inflamed tissue, are however situations with which surgeons are not very familiar.

These factors, together with the dehiscence from wounds and the inherent ischaemias caused by sutures placed very close together, have led to the development of adhesive systems for tissues which repair the tissues in a non-traumatic way, in addition to being haemostatic.

These adhesion systems are useful for arresting bleeding from capillary vessels after major arterial and venous vessels have been ligated (parenchymatous lesions), alongside vascular sutures and in patients suffering haemorrhagic episodes. They are also useful for sealing and adhering tissues, reinforcing insufficient sutures, fixing inserts and implants and for covering sutures in order to make them impermeable to gases and liquids, among other uses.

In addition to this, these adhesion systems can be used in combination with sheets of collagen, spongy, ceramic and antibiotic materials and other biocompatible materials as supports for cell cultures (endothelial cells, keratinocytes) in the poorly-vascularised zones of cutaneous inserts, skin ulcers and necrosis due to aggressive cytotoxic therapies.

The process of blood coagulation comprises various stages of chained reactions between various proteins in blood. Sealing by fibrin (also known as fibrin adhesion or fibrin adhesive) is an example of a biological seal deriving from two components and based on the final stage of the clotting cascade. The main ingredient of the first component includes fibrinogen and the main ingredient of the second component includes thrombin, which acts as a catalyst for the clotting reaction. By mixing these two components just before use and applying the mixed components to a patient's wound, a rapid coagulation reaction is achieved which helps to seal the wound, among other uses.

Various systems for applying the two components of the fibrin adhesive based on a pair of syringes supported by a connecting member are known, for example the device disclosed by document U.S. Pat. No. 4,735,616. This device further comprises plungers connected by a connecting member which is designed to allow the two plungers to be pressed simultaneously.

Nevertheless these devices have a major disadvantage in that they do not ensure that the mixture, generally 1:1, is appropriate at the point of application, because of the fact that the plungers advance out of phase due to the difference in viscosity between the two components of the adhesive, which causes clearly different resistance to advance in the syringe, giving rise to deformation of the materials of the device, which are normally made of plastics.

In order to overcome the abovementioned problems this invention provides a device for the application of a fibrin adhesive comprising two components, the said device comprising a support for syringes comprising two parallel cylindrical housings to receive two syringes and a member connecting the plungers. This support for syringes and the said plunger connecting member are connected together, the said support for syringes comprising a passage for introduction of the plunger connecting member, the said passage being located in the space defined between the cylindrical housings in the said support for syringes, the said plunger connector having a zone with an appropriate geometry to slide within the said passage.

The said passage has a maximum amplitude at the ends and a minimum amplitude at the centre. According to preferred embodiments the said passage has the general shape of an I or X. These shapes perform the double function of permitting the plunger connecting member to pass through the passage between the cylindrical housings of the said syringe support and increase the moment of inertia of the plunger connector, making it much more resistant to any deformation.

One way of preserving the components of the fibrin adhesive may be within the syringes at a temperature below 0° C. The cylindrical housings of the syringe support of the device according to this invention are of the type which are open to the exterior, leaving the greatest possible part of the body of the syringe exposed to the environment to encourage melting of the components of the fibrin adhesive.

Furthermore, the syringe support of the device according to this invention has no components which prevent rotation of the bodies of the syringes once they have been pressed into the syringe support. This movement is necessary so that the syringes can be screwed onto the outlet body of the adhesive, which is where the two components are mixed before the adhesive is applied to the site of interest. The plunger connecting member has no components which prevent rotation of the plungers once they have been placed in the said connecting member.

The fibrin adhesive application device according to this invention ensures that the plungers of the syringes move simultaneously, without being out of phase with each other, ensuring that the adhesive is applied at its point of application in the correct proportion between the two components.

This invention will be described in greater detail below with reference to preferred embodiments and drawings which are not intended to restrict the technical scope of this invention.

DETAILED DESCRIPTION OF THE INVENTION

For a better understanding of this invention reference will be made below to details of embodiments and the accompanying drawings without this constituting a restriction on the scope of this invention.

Figure 1:
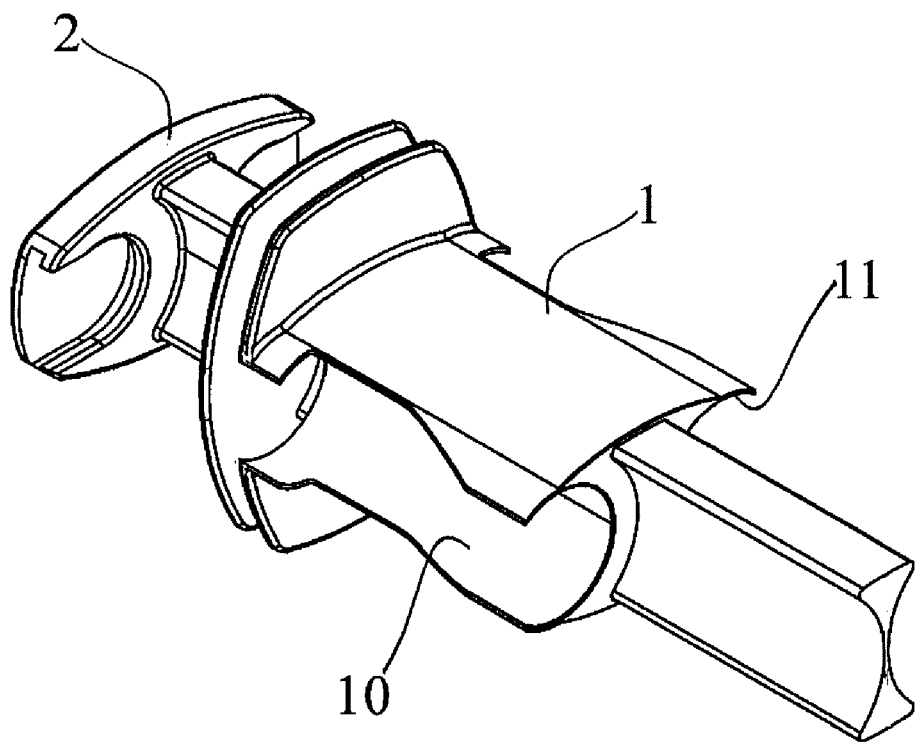
FIG. 1 shows a perspective view of an embodiment of the device for the application of two-component fibrin adhesive according to this invention.

FIG. 1 shows a perspective view of an embodiment of the device for the application of two-component fibrin adhesive according to this invention. The said device comprises a support for syringes -1- and the plunger connecting member -2-. Syringe support -1- comprises two parallel cylindrical housings -10-, -11- to receive two syringes and has the function of holding the bodies of the syringes and keeping them together in parallel in a robust manner. Preferably the said syringes are pressed into syringe support -1-. Furthermore the said syringe support has no components which prevent rotation of the said syringe bodies once the said syringes have been pressed into support -1-.

Figure 3:
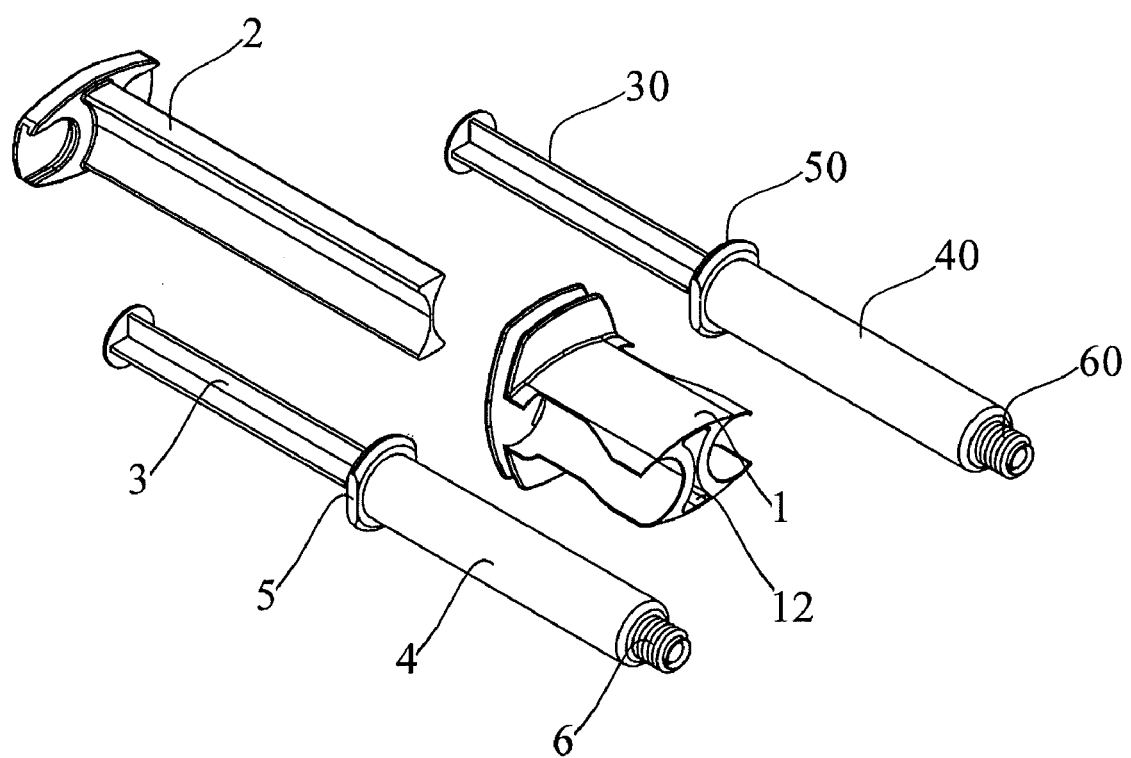
FIG. 3 shows an exploded perspective view of an embodiment of a device according to this invention together with the two syringes containing the components of the fibrin adhesive.

The syringe support of the device according to this invention is characterised in that it comprises a passage -12- for insertion and movement of the said plunger connecting member, as shown in FIG. 3, which is located in the space defined between the cylindrical housings of the said syringe support. The transverse cross-section of this passage of the syringe support has a maximum opening at the extremities and a minimum opening in the central part.

Figure 2:
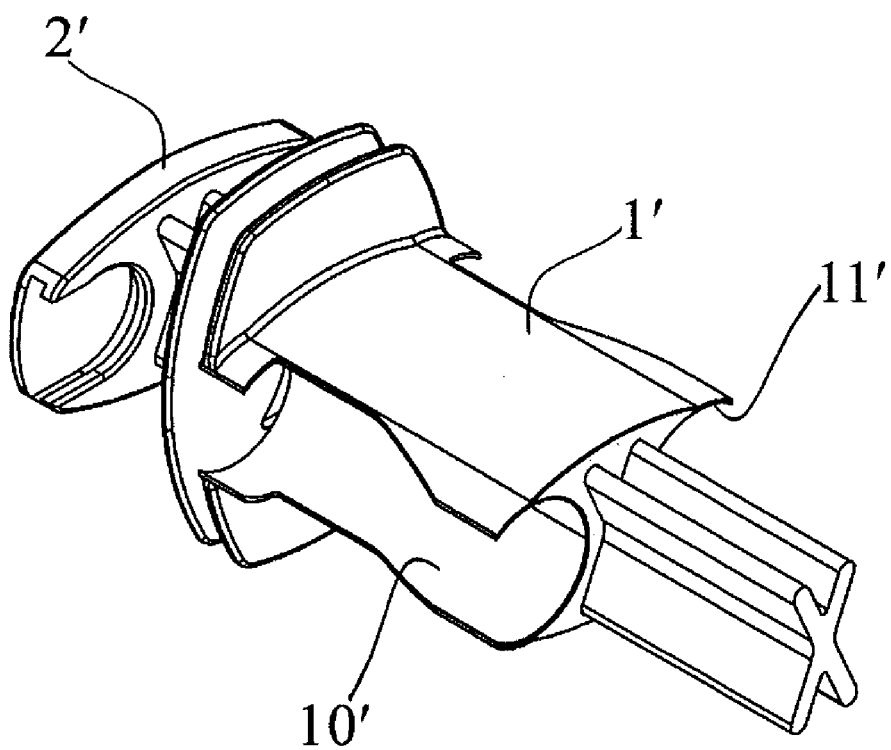
FIG. 2 shows a perspective view of a second embodiment of the two-component fibrin adhesive application device according to this invention.

In a preferred embodiment the transverse cross-section of the elongated part of the plunger connecting member has the general shape of an I (see FIG. 1), while in another preferred embodiment this elongated part of the connecting member is in the shape of an X (see FIG. 2). Both shapes are the most appropriate for ensuring robustness in the fibrin adhesive application device according to this invention.

On the other hand the connecting member has the shape of a T, as shown in FIG. 1, with a wider part which is joined at the upper extremity to a member which has suitable grooves to receive the flanges of the syringe plungers.

In the device according to this invention plunger connecting member -2-, -2'- moves within a syringe support -1-, -1'- so that the play between the two is a minimum, thus ensuring that the plungers of the syringes containing the components of the adhesive act simultaneously, that is they move without being out of phase with each other at any time until the syringes are completely discharged.

Figure 4:
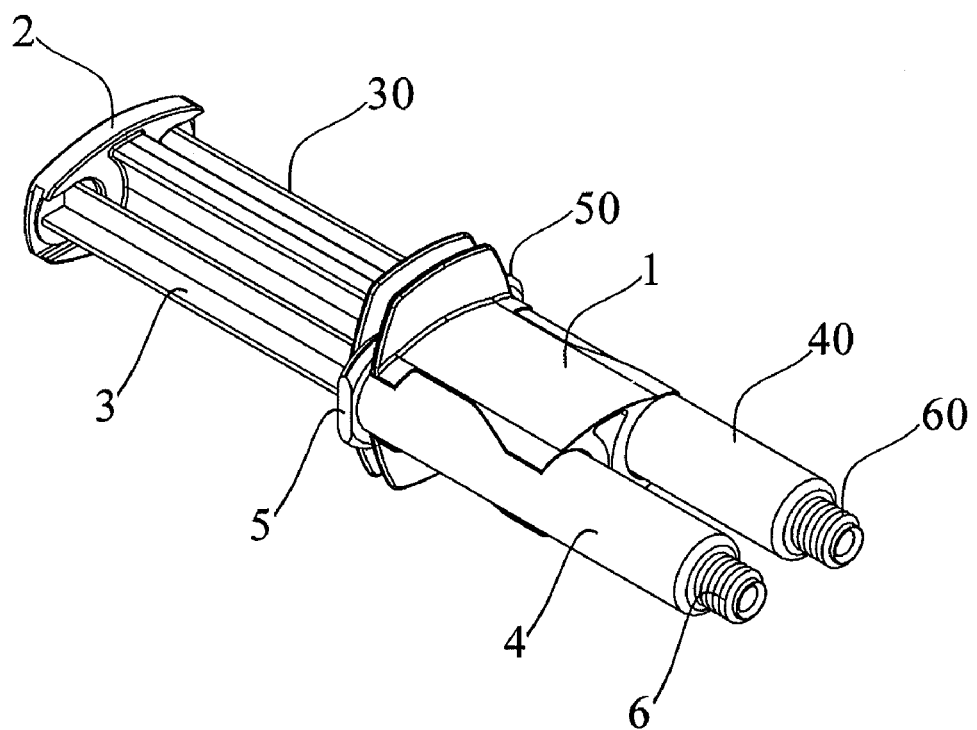
FIG. 4 shows a perspective view of the position of the two syringes in an embodiment of the device according to this invention.
Figure 5:
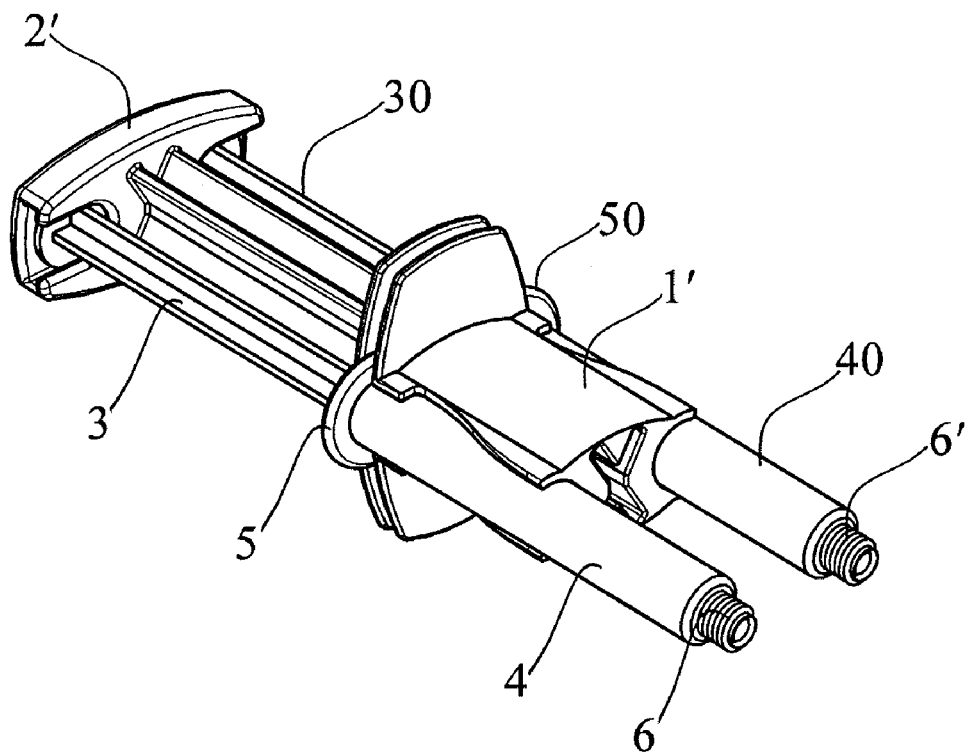
FIG. 5 shows a perspective view of the position of the two syringes in the second embodiment of the device according to this invention.

The device according to this invention is suitable for receiving a pair of syringes (see FIGS. 4 and 5) which individually contain the components of the fibrin adhesive. The syringes may be those which are normally available on the market. The diameters of these syringes may be the same or different depending upon the type of adhesive being used. Preferably the diameters of the syringes are the same.

Preferably, each syringe comprises a syringe body -4-, -40- and a plunger -3-, -30-, preferably of the piston type. Said syringe body preferably comprises a part in the form of flanges -5-, -50- at the upper extremity and another part in the form of a thread -6-, -60- at the other extremity. Syringe body -4-, -40- is pressed into syringe support -1-, -1'- and once fitted syringe support -1-, -1'- allows the syringes to rotate. In turn plunger -3-, -30- of the syringe is pressed into plunger connecting member -2-, -2'-, and once fitted plunger connecting member -2-, -2'- also allows said plungers -3-, -30- to rotate, that is the plunger connecting member has no components which prevent rotation of the said plungers. As used in conventional syringes, said plungers -3-, -30- are used to press and expel the components placed in the body of the syringes. Preferably the said plungers are of the piston type and are also standard members used with standard syringe bodies and preferably comprise an extremity which can be fitted within the bodies of the syringes and another extremity in the form of a flange, which is suitable for applying pressure thereto with the fingers of the hand.

Figure 6:
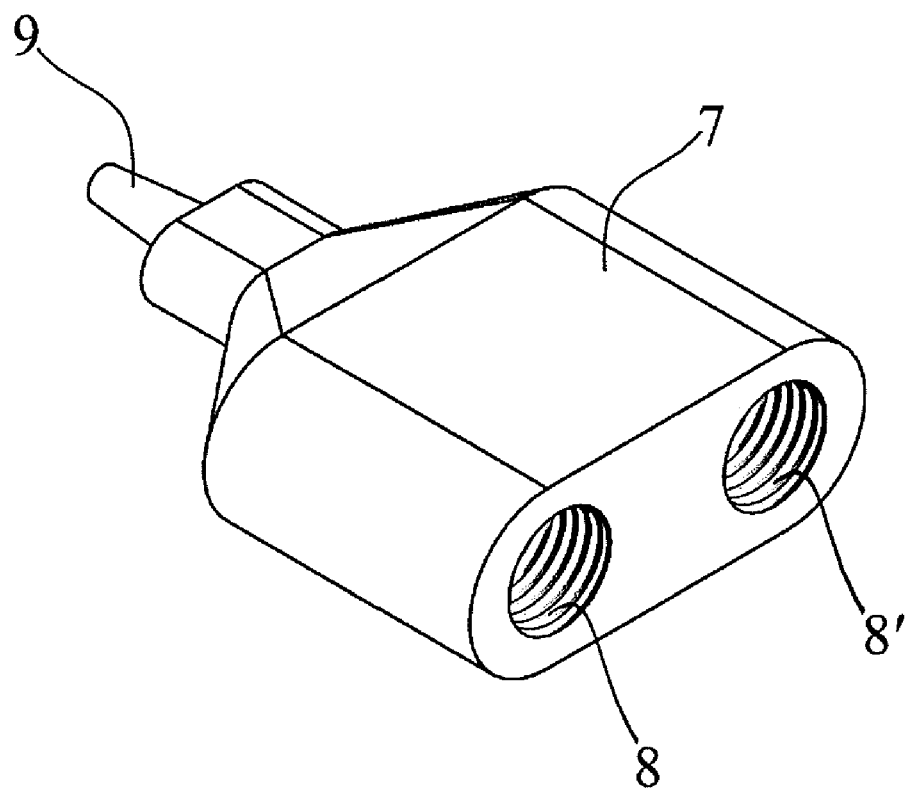
FIG. 6 shows a perspective view of an outlet body of the device according to this invention.

Preferably, the threaded portions -6-, -60- of the bodies of syringes -4-, -40- are used to provide a screwed connection between the syringes and an outlet body -7-. FIG. 6 shows an outlet body -7- in which the two components of the adhesive expelled from the syringe bodies are mixed and assists application of the said mixture. In another preferred embodiment the syringes may be press-fitted into the outlet body.

Preferably, said outlet body -7- comprises zones for screwing in syringes -8-, -8"- and an outlet zone -9- for the mixed adhesive.

Figure 7:
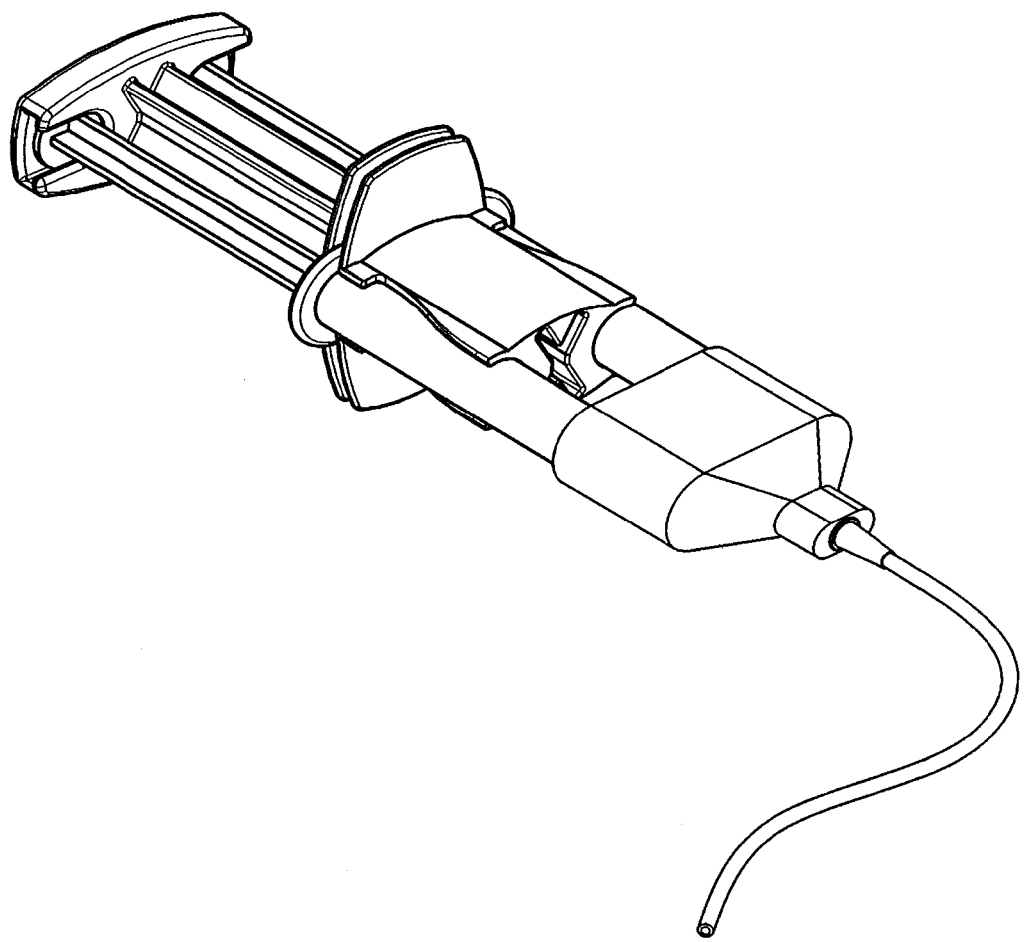
FIG. 7 shows a perspective view of an embodiment of the device according to this invention with the syringes and the outlet body connected together.
Figure 8:
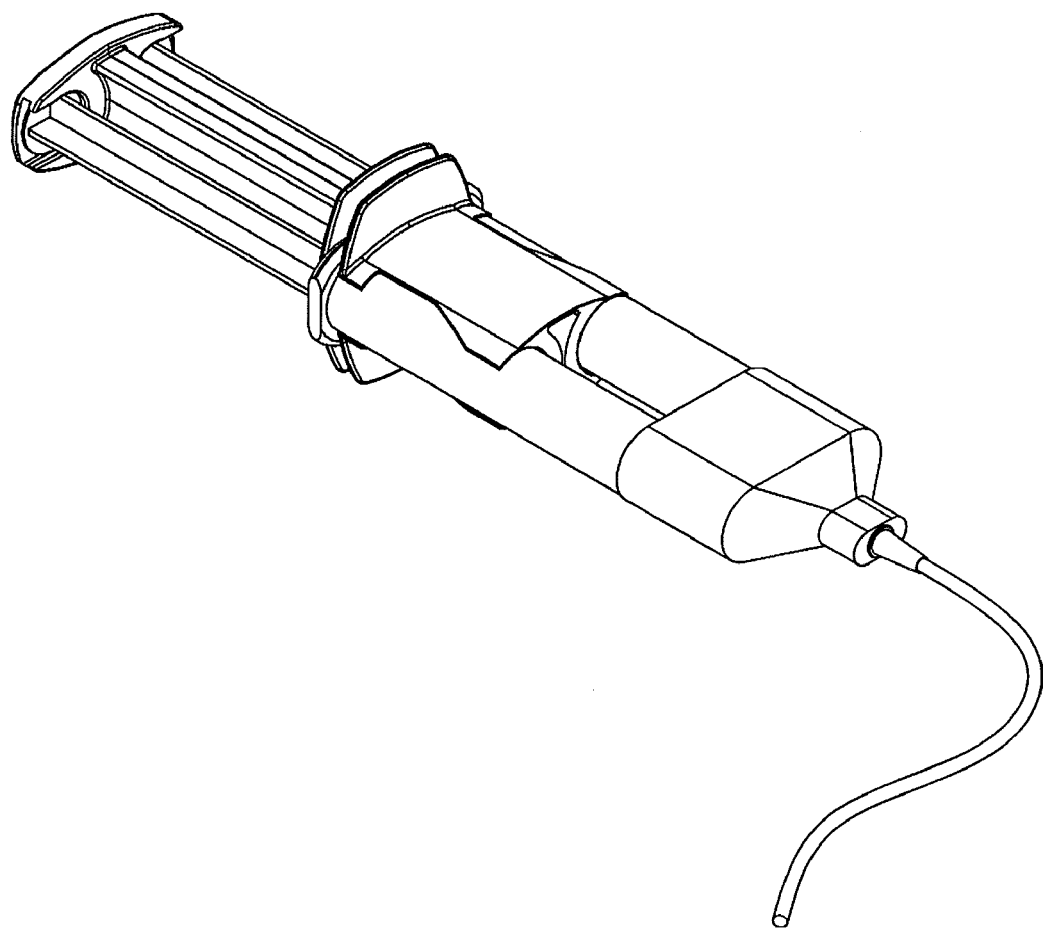
FIG. 8 shows a perspective view of the second embodiment of the device according to this invention with the syringes and the outlet body joined together.

FIGS. 7 and 8 show two embodiments of the device for the application of fibrin adhesive according to this invention once the syringes and the outlet body have been fitted.

The invention claimed is:

1. A device for the application of two components of fibrin adhesive at a treatment site which comprises:
   a support for syringes which comprises two parallel cylindrical housings extending along a longitudinal axis to receive corresponding syringes, and
   a plunger connecting member,
   wherein the support for syringes comprises a passage extending parallel to said two parallel cylindrical housings for insertion of the plunger connecting member, the passage being located in the space between the cylindrical housings of the syringe support, the plunger connecting member having a zone with a suitable geometry to slide into the passage and in that the passage defines a cross-section transverse to the longitudinal axis having a maximum size at a top and a bottom thereof and a minimum size at a center thereof.

2. A device according to claim 1, wherein the transverse cross-section of the zone through which the plunger connecting member moves within the syringe support has the general shape of an I.

3. A device according to claim 1, wherein the transverse cross-section of the zone through which the plunger connecting member moves within the syringe support has the general shape of an X.

4. A device according to claim 1, wherein the syringe support comprises two housings of cylindrical shape suitable to receive standard syringes, the syringes being pressed into the housings.

5. A device according to claim 1, wherein the syringe support has no components which will impede rotation of the bodies of the syringes once the syringes have been pressed into the syringe support.

6. A device according to claim 1, wherein the plunger connecting member has no components which prevent rotation of the plungers once the plungers have been fitted in the plunger connecting member.

7. A device according to claim 1, wherein the device also comprises an outlet body which is connected to the bodies of the syringes of the fibrin adhesive by screwing.

8. A device according to claim 1, wherein the syringes have an upper part in the form of a flange and a lower part in the form of a thread.

9. A device according to claim 1, wherein the syringes have the same diameter and volume.

10. A device according to claim 2, wherein the syringe support comprises two housings of cylindrical shape suitable to receive standard syringes, the syringes being pressed into the housings.

11. A device according to claim 3, wherein the syringe support comprises two housings of cylindrical shape suitable to receive standard syringes, the syringes being pressed into the housings.

12. A device according to claim 2, wherein the syringe support has no components which will impede rotation of the bodies of the syringes once the syringes have been pressed into the syringe support.

13. A device according to claim 3, wherein the syringe support has no components which will impede rotation of the bodies of the syringes once the syringes have been pressed into the syringe support.

14. A device according to claim 4, wherein the syringe support has no components which will impede rotation of the bodies of the syringes once the syringes have been pressed into the syringe support.

15. A device according to claim 2, wherein the plunger connecting member has no components which prevent rotation of the plungers once the plungers have been fitted in the plunger connecting member.

16. A device according to claim 3, wherein the plunger connecting member has no components which prevent rotation of the plungers once the plungers have been fitted in the plunger connecting member.

17. A device according to claim 4, wherein the plunger connecting member has no components which prevent rotation of the the plungers once the the plungers have been fitted in the plunger connecting member.

18. A device according to claim 5, wherein the plunger connecting member has no components which prevent rotation of the plungers once the plungers have been fitted in the plunger connecting member.

19. A device according to claim 2, wherein the device further comprises an outlet body which is connected to the bodies of the syringes of the fibrin adhesive by screwing.

20. A device according to claim 3, wherein the device further comprises an outlet body which is connected to the bodies of the syringes of the fibrin adhesive by screwing.

* * * * *